(12) United States Patent
Rodriguez et al.

(10) Patent No.: US 8,337,926 B2
(45) Date of Patent: Dec. 25, 2012

(54) USE OF 4-KETOLUTEIN AS A FOOD ADDITIVE FOR EGG YOLK COLORATION

(75) Inventors: Gustavo Rodriguez, Los Mochis (MX); George Schloemer, Longmont, CO (US); Alejandro Diaz, Los Mochis (MX)

(73) Assignee: DSM IP Assets B.V., Heerlen (NL)

( * ) Notice: Subject to any disclaimer, the term of this patent is extended or adjusted under 35 U.S.C. 154(b) by 1125 days.

(21) Appl. No.: 11/632,530

(22) PCT Filed: Jul. 11, 2005

(86) PCT No.: PCT/EP2005/007479
§ 371 (c)(1),
(2), (4) Date: Jan. 17, 2007

(87) PCT Pub. No.: WO2006/008016
PCT Pub. Date: Jan. 26, 2006

(65) Prior Publication Data
US 2007/0254082 A1    Nov. 1, 2007

Related U.S. Application Data

(60) Provisional application No. 60/589,628, filed on Jul. 21, 2004.

(51) Int. Cl.
*A23L 1/27*     (2006.01)
*A23L 1/30*     (2006.01)
(52) U.S. Cl. .......................................... 426/540; 426/73
(58) Field of Classification Search .................. 426/47, 426/73, 330.1, 558, 568, 614, 623, 644, 540
See application file for complete search history.

(56) References Cited

U.S. PATENT DOCUMENTS 5,849,345 A * 12/1998 Giger et al. ....................... 426/2
5,973,211 A   10/1999 Rodriguez
6,372,946 B1   4/2002 Schloemer et al.
6,582,721 B1 *  6/2003 Lang ............................... 424/439

FOREIGN PATENT DOCUMENTS

JP    2003-102395       4/2003
WO    WO 2004/039991 A2   5/2004

OTHER PUBLICATIONS

NPL "Xanthophyll and Yellow orange" retrieved on Jun. 5, 2011.*
NPL "Ketolutein and color" in "Animal Biochromes and Structural Colours" by Denis L. Fox (2nd ed.), p. 404, 1976. ISBN 0-520-02347-1.*
Sakaguchi et al, "Oxidation of Diols and Ethers by $NaBrO_3/NaHSO_3$ Reagent", Bulletin of the Chemical Society of Japan, Chemical Society of Japan, Tokyo, JP, vol. 70, No. 10, 1997, pp. 2561-2566.
Cooper et al, "Cartenoids and related compound. Part XXXII, Synthesis of astaxanthin, phoenicoxanthin, hydroxyechinenone, and the corresponding diosphenols", Journal of the Chemical Society, Letchworth, GB, No. 21, 1975, pp. 2195-2204.
Database Caplus Chemical Abstract Service, Columbus, Ohio, US; XP002352540 & Y. Tanaka, "Comparative biochemical studies on carotenoids in aquatic animals", Kagoshima Daigaku Suisangakubu Kiyo, vol. 27, No. 2, 1978, pp. 355-422.
Database Caplus Chemical Abstracts Service, Columbus, Ohio, US; XP002352541 & B. Czeczuga et al, "Rapeseed meal in the diet of common carp reared in heated waters", Zeitschrift Fuer Tierphysiologie, Tierernaehrung Und Futtermittelkunde, vol. 50, No. 1-2, 1983, pp. 52-61.
Database Caplus Chemical Abstracts Service Columbus, Ohio, US; XP002352542 & M. Hata et al, "Carotenoid pigments in goldfish, IV. Carotenoid metabolism", Nippon Suisan Gakkaishi, vol. 38, No. 4, 1972, pp. 331-338.
Database Caplus Chemical Abstracts Service Columbus, Ohio, US; XP002352543 & M. Tsushima et al, "Carotenoid composition and two new 4-ketolutein isomers in the integuments of the red tilefish Branchiostegus japonicus", Fisheries Science, vol. 64, No. 6, 1998, pp. 464-468.
International Search Report mailed Nov. 16, 2005 in PCT/EP2005/007479.
Written Opinion mailed Nov. 16, 2005 in PCT/EP2005/007479.
Hata et al, "Carotenoid Pigments in Goldfish-IV. Carotenoid Metabolish," Bulletin of the Japanese Society of Scientific Fisheries, vol. 38, No. 4, (1972), pp. 331-338.
Tanaka, "Comparative Biochemical Studies on Carotenoids in Aquatic animals," Mem., Fac., fish, Kagoshima University, vol. 27, No. 2 (1978), pp. 355-422.
Hata et al, "Carotenoid Pigments in Goldfish (Carassius Auratus)," Int. J. Biochem., 2, (1971), pp. 11-19.

* cited by examiner

*Primary Examiner* — Humera Sheikh
*Assistant Examiner* — Bhaskar Mukhopadhyay
(74) *Attorney, Agent, or Firm* — Nixon & Vanderhye P.C.

(57) ABSTRACT

A method of obtaining yellow-orange coloration of egg yolks and chicken skins using 4-ketolutein as feed additive for chicken feed.

5 Claims, No Drawings

USE OF 4-KETOLUTEIN AS A FOOD ADDITIVE FOR EGG YOLK COLORATION

This application is the US national phase of international application PCT/EP2005/007479 filed 11 Jul. 2005 which designated the U.S. and claims benefit of U.S. 60/589,628, dated 21 Jul. 2004, the entire content of which is hereby incorporated by reference.

BACKGROUND OF THE INVENTION

1. Field of the Invention

Chemical synthesis of 4-ketolutein is described. The synthesized compound is useful in the coloration of chicken egg yolks.

2. Description of the Related Art

Lutein is commercially produced in large quantities from marigold flowers (*Tagetes erecta*) for use as a food additive. Specifically it is used widely to color chicken egg yolks. However, while lutein imparts a strong yellow color to the yolk, it is desirable in many markets to add red coloration so that the resulting egg yolk is more orange in color. Typically this red coloration is obtained by the addition of paprika extract or canthaxanthin to the feed. Addition of these extracts to the feed significantly increases the expense. Thus, there is a need for a lutein product which can impart the desired coloration without subsequent addition of other colorants. If one could economically modify lutein itself to produce the desired orange-red coloration, there would be no need to add expensive extracts to achieve the desired effect. This, in fact, is the basis of our present invention.

Previously we have demonstrated a mild oxidative procedure for the conversion of zeaxanthin to astaxanthin (U.S. Pat. Nos. 5,973,211 and 6,329,557). We now have demonstrated a similar procedure for the conversion of lutein to 4-ketolutein in good yield. Mixtures of 4-ketolutein and lutein, which can be obtained by partial oxidation or by subsequent mixing of lutein with the 4-ketolutein obtained, demonstrate excellent coloration of egg yolks in trials.

Lutein is obtained in good purity by hydrolysis of the lutein esters extracted from Marigold flowers. It is semi-purified by several means and is sold for formulation into chicken feed where it imparts a yellow coloration to the egg yolk and also to the skin. However, chickens raised under native conditions generally consume other carotenoids which will impart some red coloration to the egg yolk. Therefore it is desirable to simulate this coloration through the use of mixtures of lutein with other carotenoids which possess reddish coloration.

The conversion of lutein to 4-ketolutein is shown in the following diagram:

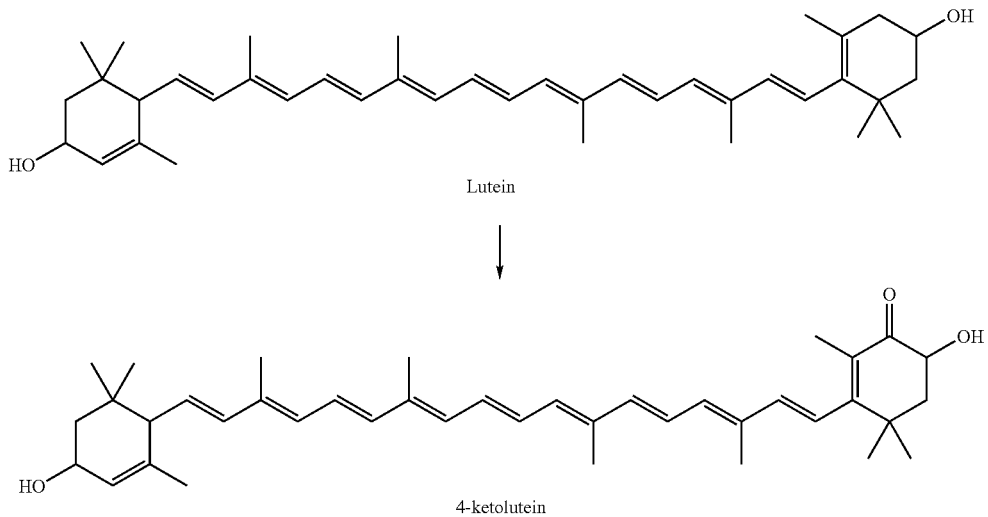

Lutein 4-ketolutein

SUMMARY OF THE INVENTION

Embodiments of the invention are directed to a method of preparing 4-ketolutein of Formula (I) from lutein comprising the steps of dissolving lutein in an organic solvent, reacting the lutein with an oxidizing agent to produce 4-ketolutein, and separating 4-ketolutein from the reaction mixture.

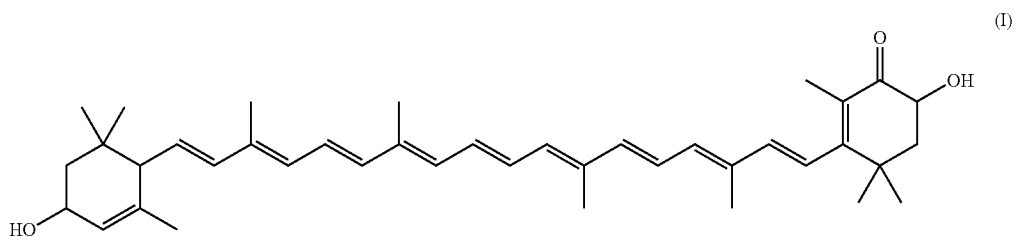

(I)

Preferably, the organic solvent is a halogenated organic solvent. More preferably, the halogenated organic solvent is chloroform. In preferred embodiments, the weight/volume ratio of the organic solvent to lutein is between 5 to 40 parts for each one.

In preferred embodiments, the oxidizing agent is produced by mixing a saturated aqueous solution which may be sodium sulfite, potassium sulfite, sodium hydrogen sulfite, potassium hydrogen sulfite, sodium bisulfite or potassium bisulfite, with a saturated solution of a bromate salt. More preferably, the oxidizing agent is produced by mixing a saturated aqueous solution of sodium bisulfite with a saturated solution of sodium bromate. In preferred embodiments, the weight ratio of sodium bisulfite to the sodium bromate is about 1.5:1.

In another preferred embodiment, the oxidizing agent is produced by mixing a saturated aqueous solution of sodium bisulfite with a saturated solution of potassium bromate. In another preferred embodiment, the oxidizing agent is produced by mixing a saturated aqueous solution of sodium bisulfite with a saturated solution of calcium bromate. In another preferred embodiment, the oxidizing agent is produced by mixing a saturated aqueous solution of sodium bisulfite with a saturated solution of cerium bromate. In preferred embodiments, the weight ratio of the oxidizing agent to lutein is between 0.5 to 5 parts for each part of carotenoid. In preferred embodiments, the pH of the aqueous oxidizing agent is between 1 to 4. In preferred embodiments, the reaction temperature is between 2 to 10° C.

In preferred embodiments, lutein is obtained by saponification of a plant extract. Preferably, the plant is marigold. In alternate preferred embodiments, lutein is prepared synthetically.

Embodiments of the invention are directed to a method of using 4-ketolutein of structure 1 as an animal feed additive. In preferred embodiments, the animal is a chicken egg layer and the 4-ketolutein is added to the feed. In preferred embodiments, the 4-ketolutein is added to the feed in an amount sufficient to produce a concentration of 4-ketolutein product of between about 1 to 80 ppm. Preferably, the 4-ketolutein is added to the feed of a chicken egg layer in an amount sufficient to produce a concentration of 4-ketolutein product in the feed of the chicken egg layer of between about 2-10 ppm. More preferably an amount of lutein is added to the feed in combination with 4-ketolutein in an amount sufficient to produce a concentration of lutein in the feed of 2-3 ppm lutein.

Embodiments of the invention are directed to a method of using 4-ketolutein as an animal feed additive where the 4-ketolutein is prepared by dissolving lutein in an organic solvent, reacting the lutein with an oxidizing agent to produce 4-ketolutein, and separating 4-ketolutein from the reaction mixture.

Further aspects, features and advantages of this invention will become apparent from the detailed description of the preferred embodiments which follow.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

Preferred embodiments of the invention are directed to an oxidation procedure for conversion of lutein to 4-ketolutein. We have discovered that by a simple oxidation procedure, lutein can be converted in good yields to 4-ketolutein which, in fact, possesses the desirable reddish coloration.

This oxidation procedure can be carried out in various ways such that only the desired side of the molecule is affected. Suitable conditions are halogenating conditions in a mixed aqueous/organic medium or peroxides. These halogenating agents can be bromine, NBS or similar agent. Likewise conditions known to impart hydroxylation alpha to olefins can be employed. Non-limiting examples of performing allylic oxidations or agents that may be employed in oxidation reactions have been reviewed in the major reference books by Trost and Larock, "Comprehensive Organic Synthesis," Volume 7, Pergamon Press, New York 1991, pages 83-117, and Richard C. Larock "Comprehensive Organic Transformations," Wiley-VCH, New York, 1999, pages 1207-1209, which are incorporated herein in their entirety by reference.

In preferred embodiments, mixtures of bromates and bisulfites are used as the oxidizing agent. In preferred embodiments, these reactions are carried out in two-phase conditions employing an aqueous media and an unreactive immiscible organic media. The bromates used generally are sodium or potassium bromate with sodium or potassium bisulfite or meta-bisulfite. The bromates and bisulfites can either be mixed during the reaction or immediately prior to the reaction. In a most preferred embodiment, a bromate/bisulfite mixture is prepared which is then added slowly to a slurry of lutein in an organic solvent. In a preferred embodiment, a saturated aqueous solution of sodium bisulfite is reacted with a saturated solution of sodium bromate in a ratio of about 1-3:1, preferably about 1.0 to 1.5:1 with moderate mixing.

Any unreactive immiscible organic media may be used as the organic solvent as long as it is a solvent which can dissolve lutein. In preferred embodiments, the solvent is chloroform.

Preferably, the reaction is carried out at any temperature between 0° C. and 70° C. More preferably, the reaction is carried out at temperatures between 2 and 10° C.

The carotenoid product may be separated from the reaction mixture by extraction into the organic phase. Optionally, the organic phase may be washed after extraction of the product.

The carotenoids may be used as a mixture of unreacted lutein plus 4-ketolutein. The purified 4-ketolutein may be combined with lutein and/or other carotenoids to provide the desired coloration. In preferred embodiments, the 4-ketolutein obtained by the described method is added to animal feed to provide desirable coloration in the resulting food products. In preferred embodiments, compositions including 4-ketolutein prepared by the described method are used as a chicken feed additive to achieve desirable yellow-orange coloration of chicken skin and/or egg yolks. The 4-ketolutein product may also be added directly to foods to provide desirable coloration.

EXAMPLE

In a suitable vessel, 1 Kg of marigold extract containing 106 grams of carotenoids, of which 90 grams correspond to lutein was slurried, and 180 grams sodium hydroxide in 180 ml of water was added. The mixture was heated to 103° C. with stirring for one hour. After completion of saponification, 18 liters of hexane were added and the mixture was stirred. The hexane layer was separated and the aqueous layer was heated to 50° C. under 140 mm Hg absolute pressure. The aqueous layer was treated with 1.4 liters of 25% phosphoric acid which neutralized the solution to approximately pH=4. The saponified extract separated and the aqueous salt layer was removed. The organic layer was mixed with 12,800 ml of chloroform and 7.2 grams of iodine and the temperature adjusted to 5° C. Then this mixture was treated with a solution prepared by mixing 1200 ml of water, 53.6 grams of sodium bromate, 24.3 grams of sodium carbonate, 29.2 grams of sodium metabisulfite and 48.6 grams of citric acid, which was added in a lapse of one hour with continuous stirring and keeping a constant temperature of 5° C. The reaction proceeded further for two hours to the point where more than 98% of the lutein was converted to 4-ketolutein as determined by HPLC analysis. At this point the reaction was quenched by adding 1,400 ml of a 28% solution of sodium carbonate. The mixture was stirred for 10 minutes at 25° C. and then 1,400 ml of water were added and mixed for another 5 minutes. The mixture was then allowed to settle for a phase separation. The aqueous phase was separated and work continued with the organic phase eliminating the solvent using a vacuum of 640 mm Hg at 45° C. Once the solvent was eliminated, 200 grams of Tween-80 were incorporated to the concentrate at 40° C. and emulsified adding water up to a volume of 12.7 liters. The product that was obtained contained 5.1 gr/kg of total carotenoids of which 57% was 4-ketolutein. The yield of total carotenoids to starting material was 60% and the yield of 4-ketolutein from lutein was 41%.

It will be understood by those of skill in the art that numerous and various modifications can be made without departing from the spirit of the present invention. Therefore, it should be clearly understood that the forms of the present invention are illustrative only and are not intended to limit the scope of the present invention.

The invention claimed is:

1. A method of obtaining yellow-orange coloration of egg yolks from a chicken egg layer comprising feeding a chicken egg layer a feed comprising 4-ketolutein of Formula I as an additive in an amount sufficient to achieve a yellow-orange coloration of the egg yolks produced by the chicken:

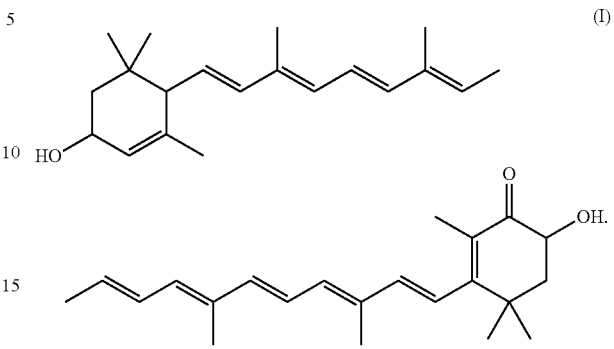

(I)

2. The method claim 1, wherein the 4-ketolutein is present in the feed in an amount sufficient to produce a concentration of 4-ketolutein of between about 1 to 80 ppm.

3. The method of claim 1, wherein the 4-ketolutein present is in the feed in an amount sufficient to produce a concentration of 4-ketolutein of between about 2-10 ppm.

4. The method of claim 3, wherein the feed further comprises lutein in an amount sufficient to produce a concentration of lutein in the feed of 2-3 ppm lutein.

5. The method claim 4, wherein the 4-ketolutein is present in the feed in an amount sufficient to produce a concentration of 4-ketolutein of between about 2 to 10 ppm.

* * * * *